(12) United States Patent
McCary et al.

(10) Patent No.: US 12,419,784 B2
(45) Date of Patent: Sep. 23, 2025

(54) ULTRASONIC SURGICAL ASPIRATION NEEDLE ASSEMBLY WITH MOLDED HUB

(71) Applicant: BAUSCH & LOMB INCORPORATED, Rochester, NY (US)

(72) Inventors: Brian D. McCary, Clayton, MO (US); Todd Smith, Sharpsburg, GA (US)

(73) Assignee: BAUSCH & LOMB INCORPORATED, Rochester, NY (US)

( * ) Notice: Subject to any disclaimer, the term of this patent is extended or adjusted under 35 U.S.C. 154(b) by 658 days.

(21) Appl. No.: 17/881,170

(22) Filed: Aug. 4, 2022

(65) Prior Publication Data

US 2022/0409432 A1    Dec. 29, 2022

Related U.S. Application Data

(62) Division of application No. 15/142,932, filed on Apr. 29, 2016, now Pat. No. 11,484,441.

(51) Int. Cl.
  *A61F 9/007*    (2006.01)
(52) U.S. Cl.
  CPC ................................ *A61F 9/00745* (2013.01)

(58) Field of Classification Search
  CPC ............. A61F 9/00745; A61F 9/00736; A61B 17/320068; A61M 1/774; A61M 1/84; A61M 5/3293; A61M 5/343; A61M 5/34
  See application file for complete search history.

(56) References Cited

U.S. PATENT DOCUMENTS

| | | | |
|---|---|---|---|
| 2014/0107565 A1* | 4/2014 | Wiljanen | A61F 9/00736 604/35 |
| 2016/0100982 A1* | 4/2016 | McCary | A61M 5/3293 604/264 |

* cited by examiner

*Primary Examiner* — Laura A Bouchelle
(74) *Attorney, Agent, or Firm* — Harness, Dickey & Pierce, P.L.C.

(57) ABSTRACT

A surgical needle assembly for attachment to an ultrasonic handpiece includes an elongated metal cannula having a distal end and a proximal end. A hub is insert molded onto the cannula generally towards the cannula proximal end and formed from a material having an ultimate strength at least twice a peak cyclical stress force at a joint between the elongated metal cannula and the hub when the surgical needle assembly is in use with the ultrasonic handpiece. The hub material has a stiffness sufficient to limit a motion of the elongated metal cannula to less than 1.5 times an expected peak to peak stroke length when the surgical needle assembly is in use with the ultrasonic handpiece. The hub includes structure for mating attachment to the ultrasonic handpiece.

21 Claims, 4 Drawing Sheets

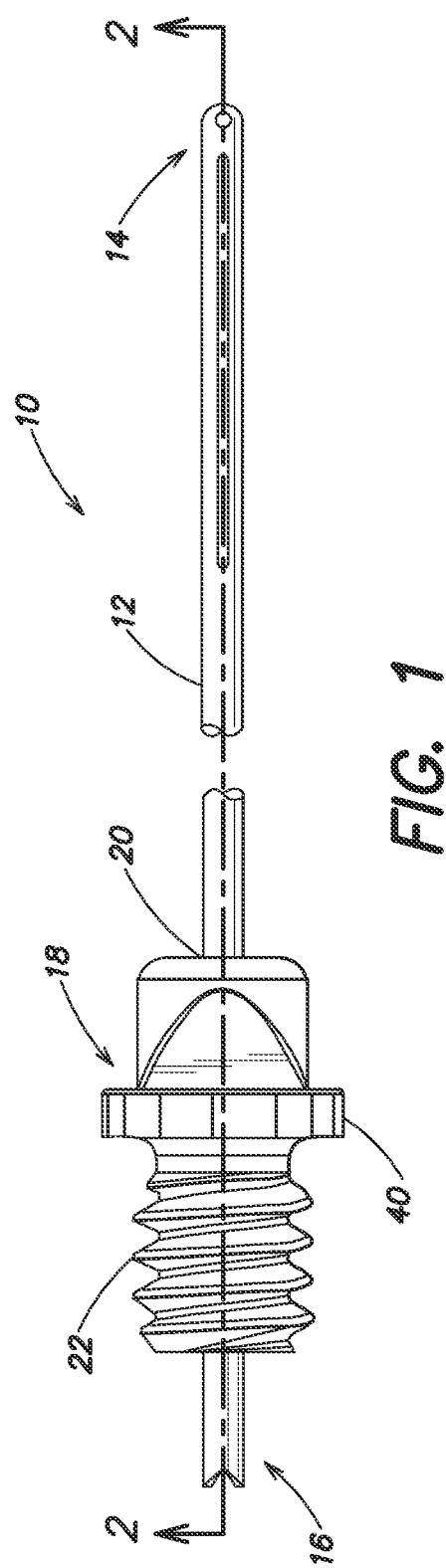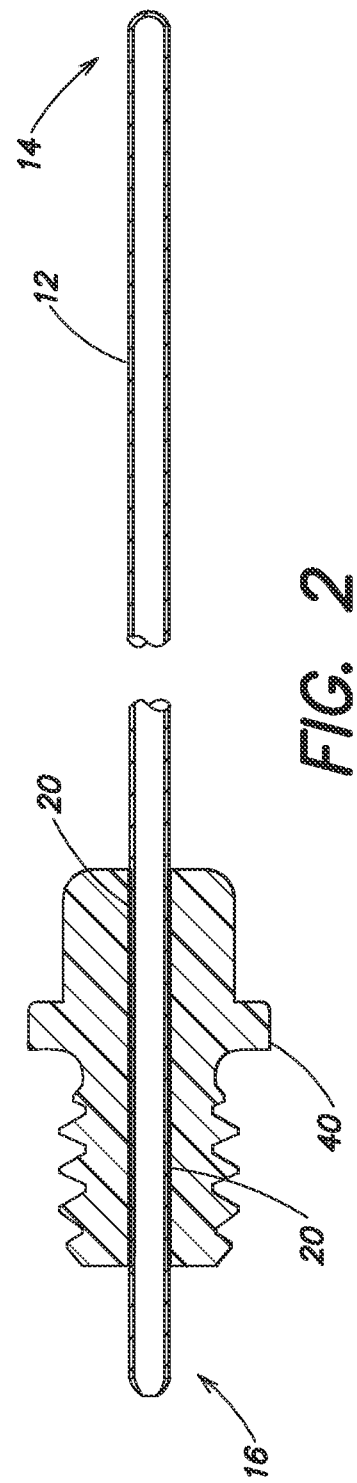

ULTRASONIC SURGICAL ASPIRATION NEEDLE ASSEMBLY WITH MOLDED HUB

FIELD

The present disclosure relates to ultrasonic surgical aspiration needle assemblies. More particularly, the present disclosure relates to ultrasonic needle assemblies having a metal needle or cannula molded to a hub that is for attachment to an ophthalmic surgical handpiece.

BACKGROUND

This section provides background information related to the present disclosure which is not necessarily prior art.

The hub and shaft portions of ultrasonic phacoemulsification (phaco) needle assemblies used in, for example cataract surgery, typically are machined monolithically out of a rigid metal, most commonly titanium. Soft compliant tips have been proposed for the distal end of phaco cannula shafts, but the use of non-metal materials for the hubs has not been proposed. The metal hub and metal cannula shaft are rigid and strong enough to withstand the forces exerted by ultrasonic vibration and to efficiently transmit the ultrasonic vibrations from a vibration source through the hub and cannula for emulsifying tissue at the distal end of the needle assembly.

Molding materials, such as polymers, are more compliant than metal and are less efficient in transferring ultrasonic energy compared to metal. Multi-part irrigation (non-vibrating) needle assemblies have been proposed that included a compliant o-ring between a substantially straight shaft and a larger hub, but these are not intended to transmit ultrasonic energy. In addition, it is also known for injection needle assemblies to have a hub molded on a metal needle; again these needle assemblies are not intended to transmit ultrasonic energy and there is no indication that such needle assemblies would withstand ultrasonic vibration.

Machining a hub and needle assembly is expensive and becomes increasingly expensive and difficult as the cannula outer diameter becomes smaller, as the cannula length becomes longer, and as the cannula wall thickness becomes thinner. The difficulty of machining a hub and needle assembly was experienced when attempting to build needle assemblies for posterior ultrasonic vitreous removal described in co-pending U.S. patent application Ser. No. 14/020,386 entitled Vibrating Surgical Device for Removal of Vitreous and Other Tissue. The ultrasonic needle assembly for vitreous removal is longer than a typical phaco needle assembly to enable the needle assembly to span across the posterior segment of the eye. The ultrasonic vitreous cannula also has a smaller outer diameter (OD) compared to a typical phaco cannula to allow the vitreous needle assembly to pass through entry alignment cannulas used in sutureless posterior surgery. It is also desirable for the ultrasonic vitreous cannula to have an inner diameter (ID) as large as possible to remove vitreous as efficiently as possible. Since the OD of the vitreous cannula is limited by the entry alignment cannula, to maximize the vitreous cannula ID, it is desirable to minimize the wall thickness of the vitreous cannula.

Further, it is desirable to create an ultrasonic surgical needle assembly that is of low enough cost to be a single-use, disposable needle assembly. Producing an ultrasonic surgical needle assembly at a cost to justify a single-use needle assembly and that can accommodate especially small gauge needle assemblies of longer than standard length with thinner than normal needle assembly wall thickness would be desirable.

DRAWINGS

The drawings described herein are for illustrative purposes only of selected embodiments and not all possible implementations, and are not intended to limit the scope of the present disclosure.

FIG. 1 is an elevation of an example surgical needle assembly;

FIG. 2 is a cut away elevation of FIG. 1 along line 2-2;

Corresponding reference numerals indicate corresponding parts throughout the several views of the drawings.

DETAILED DESCRIPTION

Figure 3:
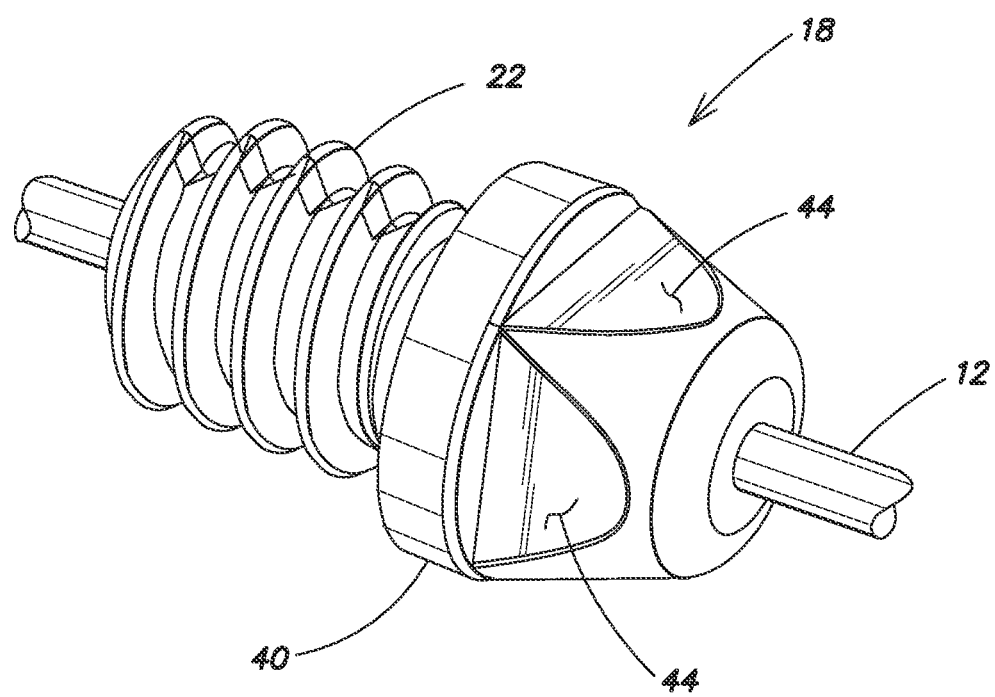
FIG. 3 is a partial perspective of FIG. 1.

Example embodiments will now be described more fully with reference to the accompanying drawings.

A surgical needle assembly 10 for attachment to an ultrasonic handpiece is shown in FIG. 1. The needle assembly 10 includes an elongated metal cannula 12 having a distal end 14 and a proximal end 16. A hub 18 is insert molded onto the cannula 12 generally towards the cannula proximal end 16 and is formed from a material having an ultimate strength at least twice a peak cyclical stress force at a joint 20 between the elongated metal cannula 12 and the hub 18 when the surgical needle assembly is in use with the ultrasonic handpiece (not shown). The hub material also has a stiffness sufficient to limit a motion of the elongated metal cannula 12 relative to portions of hub 18 to less than 1.5 times an expected peak to peak stroke length when the surgical needle assembly 10 is in use with the ultrasonic handpiece. The hub 18 also includes structure 22 for mating attachment to the ultrasonic handpiece (not shown). It is believed that hub mating structure 22 will perform best as a male structure, such as the threads shown. However, hub mating structure may also be formed as a female structure. Depending on the ultrasonic levels used, a female hub mating structure may require the use of an over-sleeve to prevent the hub from expanding and slipping as the hub material heats up during use to maintain fluid tight connection with the ultrasonic handpiece. Other mating structure besides threads may also be used.

Hub 18 may insert molded onto cannula 12 by any acceptable molding technique and may be formed from a polymer, such as polyetherimide (PEI) which is sold under the brand name Ultem™ by a variety of companies. Ultem™ HU1010 and HU1010K currently manufactured by SABIC have been found to be effective hub materials. Other materials, depending on the application may also be acceptable such as polyetherehterketone (PEEK), polyaryletherketone (PAEK), polysulfone (PSU), polyehtersulfone (PESU), polyphenylsulfone (PPSU), self-reinforced polyphenylene (SRP), polycarbonate (PC), or other suitable materials. Materials may also use fillers, such as glass, as long as they are certifiable as biocompatible. The term "insert molded" as used in this disclosure refers to the process of molding or forming plastic or other polymers around other, non-plastic, non-polymer parts (inserts). Joint 20 is best seen in FIG. 2 as the thick black line.

Cannula 12 may be formed from an appropriate biocompatible metal such as stainless steel, titanium, or nickel-titanium alloy (aka, Nitinol).

The properties of the hub polymer may be selected to improve various aspects of surgical performance. For instance, an ultimate strength of the hub material may be selected to prevent joint failure under the anticipated cyclical stresses to which the horn-hub-cannula interface will be subjected under normally anticipated operating conditions. Alternatively or additionally, a melting point of the hub polymer may be selected to be low enough to melt or deform if subjected to autoclave temperatures to prevent reuse of single use needle assemblies.

Proximal end 16 may have attachment structure formed on cannula 12 for enhancing an adhesion or grip of the hub material to cannula 12, and/or to improve the shear stiffness of the hub material. For instance, chemical etching or deposition techniques may be used to roughen the outer surface of cannula 12 (not shown). Grooves 24 (cross-hatched lines) and elevated lands 26 (diamond-shapes) of FIG. 4 may be created, e.g. using laser etching to improve the grip between cannula 12 and hub 18. Care should be taken, especially with small gauge cannulas, e.g. 23 or 25 ga., having thin walls, when etching grooves 24 because it has been found that the grooves create a stress failure location during ultrasonic operation. Deposing material onto cannula 12 (not shown) may provide a more robust solution if enhanced adhesion between cannula 12 and hub 18 is required for a particular design. Alternatively, ring sheaths 28, as shown in FIG. 5, may be attached to cannula 12 to reduce the thickness of the hub portion subjected to shear forces during use; thus enhancing the stiffness of the joint 20, and to provide axial surfaces 30 for transmitting axial push and pull forces directly to cannula 12. The ring sheaths 28 may be attached to cannula 12 by any acceptable manner, such as adhesives, welding, laser welding, crimping, etc.

Figure 4:
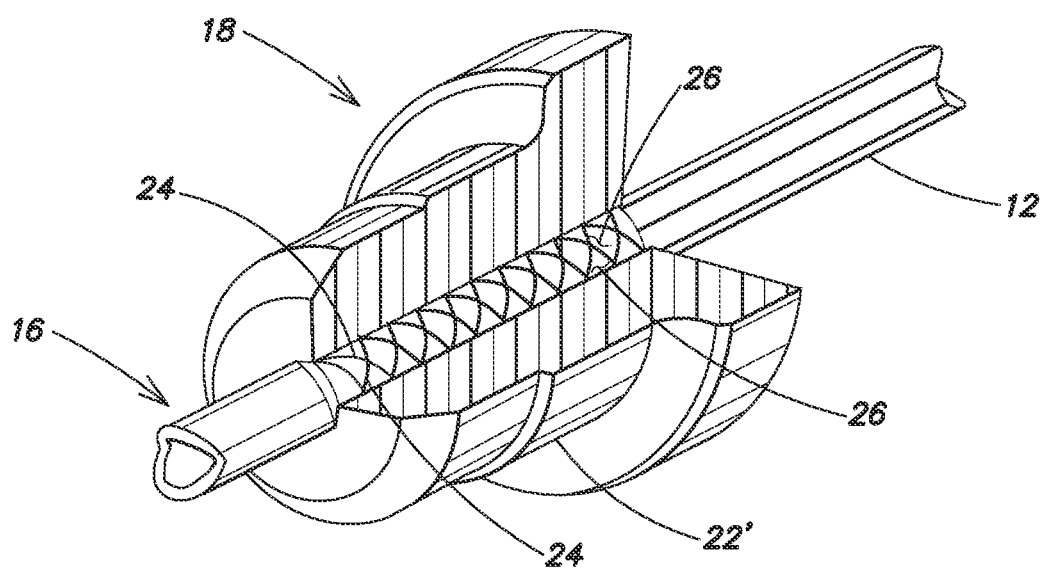
FIG. 4 is a partial perspective and partial cut away of an alternate example.
Figure 5:
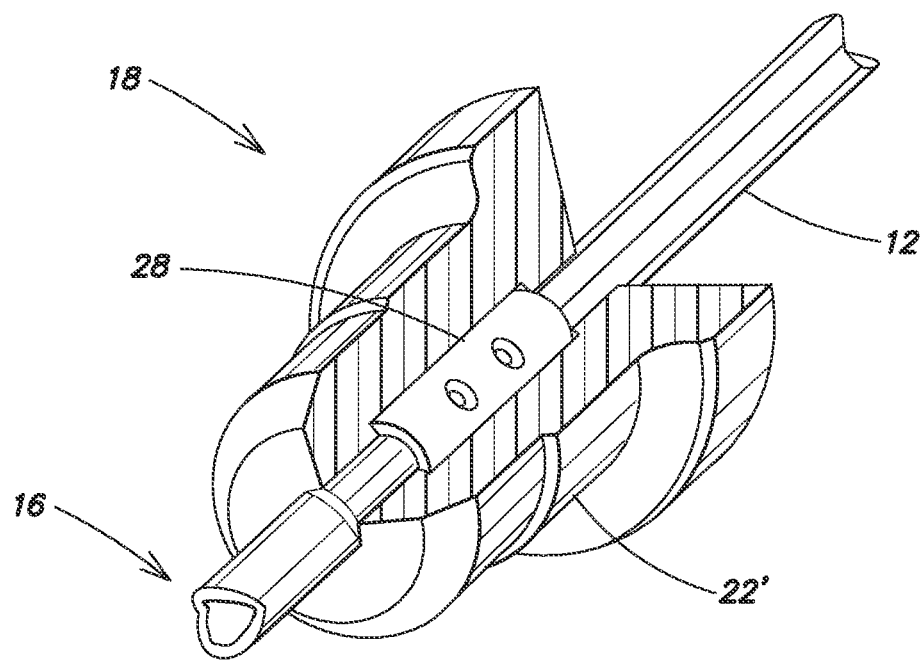
FIG. 5 is a partial perspective and partial cut away of another alternate example.
Figure 6:
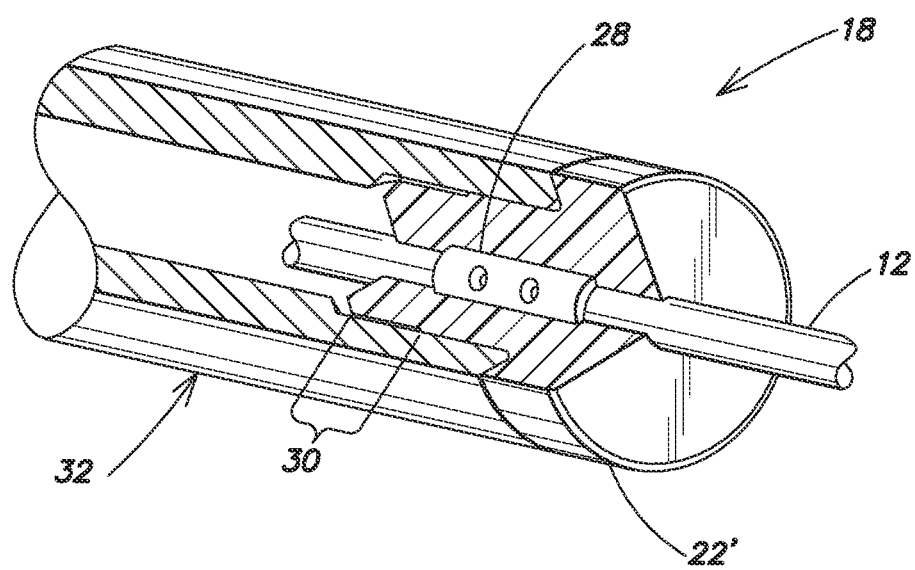
FIG. 6 is a partial perspective and partial cut away of an example surgical needle assembly attached to an ultrasonic handpiece.

The male structure 22 may include threads formed in the hub 18, as shown in FIGS. 1-3 or may include a press-fit bearing surface 22', as shown in FIGS. 4-6 for creating an interference attachment with a horn of the handpiece. As shown in FIG. 6, the male structure may also have a short section, shown generally at 30, with a smaller OD to facilitate insertion into the horn 32 during press-installation. As shown, the male structure may also have a tapered section to further facilitate the initial press installation.

Figure 7:
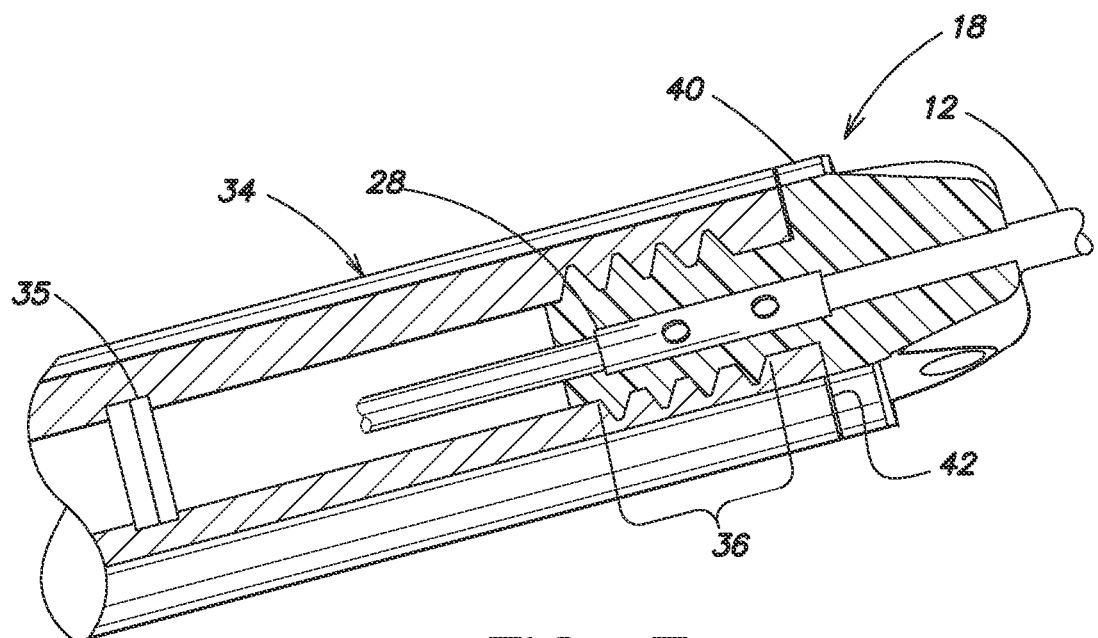
FIG. 7 is a partial perspective and partial cut away of another example surgical needle assembly attached to an ultrasonic handpiece.

If the hub 18 is threaded, the handpiece 34, shown in FIG. 7, may have a threaded section, shown generally at 36, for mating with the hub 18. The threads of handpiece 34 and hub 18 may have any acceptable type of threads to facilitate a liquid-tight seal during use. For example, the threads may have a tapered section similar to known pipe threads.

Figure 8:
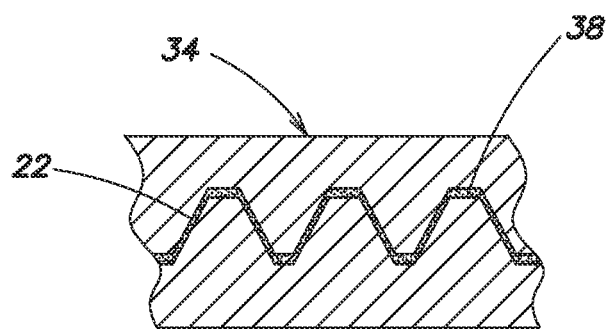
FIG. 8 is a partial view of a portion of FIG. 7.

Alternatively, when the surgical needle assembly 10 is attached to the ultrasonic handpiece 34 via threads, a thread fill material 38, as shown in FIG. 8, may be added for enhancing the attachment of the surgical needle assembly 10 to the ultrasonic handpiece 34 and enhancing a liquid-tight seal with the ultrasonic handpiece 34. The thread fill material may be any acceptable material that enhances the attachment of hub 18 to the ultrasonic handpiece 34, e.g. Loctite® M121HP or M11fl. The hub 18 may also include a flange portion 40 that is sufficiently thick for producing a liquid-tight seal with the ultrasonic handpiece 34. The flange portion 40 must be sufficiently thick to provide structural stability and not deform so that a tight seal at 42 may be formed between the flange portion 40 and the handpiece 34.

FIG. 3 provides a good perspective view of hub 18, including the wrench flats 44 for mating with a wrench to tighten the hub 18 onto a handpiece.

Producing a commercially effective ultrasonic surgical needle assembly with an insert molded hub requires that the hub meet at least two conditions. First, the hub must be strong enough to withstand the expected forces imposed by the ultrasonic vibrations under normal use. Second, the hub must be stiff enough to sufficiently limit the motion of the needle assembly under normal ultrasonic cyclical vibrations. These conditions are not expected for needle assemblies used for injections.

Details of the hub design (length, material thickness, material shear modulus and shear strength, and inclusion of interfering features such as threads, ridges, cross-holes, etc.) may affect both the stiffness and the strength of the hub.

To optimize strength, designers may specify longer hubs, which increase the hub strength by spreading the force out over a larger area to reduce stress, or select higher strength materials. Material strength is generally specified as threshold stress levels (e.g. units of pressure such as MPa (megapascals) or PSI (pounds per square inch)) at which specific undesirable effects (e.g. plastic deformation, permanent deformation, outright failure, etc.) occur in material test samples.

To optimize stiffness, designers may specify longer hubs or thinner molded hub walls, or selecting stiffer materials. Material stiffness is generally specified using one or more modulus values, which specify the material stress level required to create a known elastic deformation in the material. Higher modulus materials typically result in stiffer hubs.

As used in this disclosure, the term ultimate strength (aka tensile strength), $\sigma_{ts}$, is the maximum engineering stress (applied load divided by the original cross-sectional area of the specimen) in a uniaxial stress-strain test. For non-deformable materials, the maximum engineering stress is the nominal stress at which a round bar of the material, loaded in tension, separates. For deformable materials, the maximum engineering stress occurs at the onset of necking at strains preceding breakage (separation). For brittle solids—ceramics, glasses, and brittle polymers—the maximum engineering stress is the same as the failure strength in tension. For metals and most composites, it is larger than the yield strength, $\sigma_y$, by a factor of between 1.1 and 5 because of work hardening or, in the case of composites, load transfer to the reinforcement.

As used in this disclosure, the term endurance strength (aka fatigue strength), $S_{Nf}$, is the value of stress at which failure occurs after $N_f$ cycles. Various multipliers can be applied to account for the degradation of the hub material and/or joint over the expected use life of the needle assembly. Use of a needle assembly continuously for 5 minutes, in the cases above, results in stressing it through slightly less than 10 million cycles. Wohler curves (S-N curves) describing the effects of cyclical fatigue on the strength of a material subjected to cyclical stress for materials show how much the material strength may degrade over a given number of cycles. Thus, the designer would select the hub component design parameters to ensure that a hub will have an endurance strength after the expected number of stress cycles equal to or greater than the peak cyclical stress force experienced at the joint between the cannula and the hub.

Under normal ophthalmic ultrasonic surgical use, hub 18 is accelerating the mass of cannula 12 through the harmonic amplitude (stroke length) required for clinical effectiveness. Although cannula 12 and hub 18 are part of a larger resonant structure with a more complex acceleration profile, the maximum acceleration of the needle assembly 10 may be conveniently bounded by assuming most motion comes from the horn of the ultrasonic handpiece, and cannula 12 is a stiff mass. In this case, an upper bound for the maximum force hub 18 will experience can be calculated as $$\text{Max Expected Force} = X_0 * \text{needle assembly mass} * (\text{Harmonic frequency})^2 = X_0 m\omega^2$$

In one example case (Case A) of a cannula 12 having a 41 mm length, 0.025" OD, 0.017" ID, and a 0.004" wall made from stainless steel of density 8 g/cm$^3$, driven at 28.5 kHz (approximately 179,000 rad/sec), with a peak-to-peak stroke amplitude (length) of 40 μm ($X_0$=20 μm), the cannula mass is ~0.056 grams and the peak force is approximately 36 Newtons (about 8 lbs. force).

In a more extreme example case (Case B) of a cannula 12 having a 41 mm length, 0.025" OD, 0.013" ID, and a 0.006" wall made from stainless steel of density 8 g/cm3, driven at 28.5 kHz (approximately 179,000 rad/sec), with a peak-to-peak stroke amplitude of 60 μm ($X_0$=20 μm), the cannula mass is ~0.077 grams and the peak force is approximately 74 Newtons (about 17 lbs. force).

In practice, the thin cannula material may be much more rigid than the over molded hub, but not be perfectly rigid compared to the driving horn of the handpiece. Therefore, the amplitude of motion at hub 18 may be somewhat less than that of distal end 14, resulting in some resonant gain within cannula 12 and a corresponding reduction in the peak force at hub 18 for a given distal end 14 motion. On the other hand, because of possible cyclical fatigue, some additional margin in the needle assembly design may be useful, and needle assembly designs incapable of withstanding the peak force calculated above are likely to fail when subjected to normal expected operational stresses.

Joint strength between cannula 12 and hub 18 can be conveniently evaluated by pulling on the joint—either by hanging a weight from the cannula or the hub or by use of automated tensile strength tester, such as those provided by the company Instron®. Although the stress hub 18 under goes anchoring cannula 12 to the vibrating horn is shear stress, the overall effective forces in the needle assembly/horn system are axial or longitudinal. A simple test to ensure the needle assembly design is strong enough is to pull on the horn and needle assembly axially, close to the joint, and confirm that the joint failure point is above the peak forces identified above, in Cases A and B. This can be done on new hubs using a force multiplier (e.g. twice the expected peak cyclical stress force at joint 20) to account for cyclical degradation, or it can be done after driving the needle assembly through an appropriate number of cycles.

Pulling on a batch of Ultem® hubs with a 4-40 UNC (Unified National Coarse) thread insert molded onto a 23 gage needle assembly with an Instron® tester resulted in failure points between 25 and 50 lbs., well in excess of the required forces identified above. It has been discovered that the integrity of the molding process affected the joint strength. Hubs with lower failure points had visible internal defects, such as bubbles, while hubs with higher failure points did not have these defects.

Designers may, of course, target a higher joint strength to provide additional design margin to minimize large quantity component failure rates or the potential impact of manufacturing process changes, or to account for larger strokes or longer uses.

Stiffness of hub 18 will now be discussed. The hub can be considered as a spring, subject to Hooke's Law (Force=K*displacement). In this view, Force/K=displacement. The hub must be stiff enough that the displacement is not significant under the expected drive forces compared to the overall desired motion amplitude (stroke length). Using the relationship already identified (Force=$X_0 m\omega^2$) and requiring that the displacement across the hub under this force must be a small factor (1/N) of the desired amplitude (that is, displacement<$X_0$/N), it may be understood that the effective stiffness K of the hub is Force/displacement={$X_0 m\omega^2/(X_0/N)$} or $Nm\omega^2$.

The theoretical stiffness of a N ideal radially symmetric hub with an OD, ID, length L and material shear modulus of G can be shown to be K=2πG*L*ID/ln(OD/ID). As an example, for molded Ultem hubs with OD=0.112" (major diameter of the 4-40 thread), ID of 0.025" (minimum ID of 23 gage needle assemblies), length of 0.3" and shear modulus G of ~170 kPSI, an estimated stiffness K=5300 lbs./inch or 5.3 lbs./0.001". Axial pull testing seven samples, on an Instron® tester, suggested that the joint had a stiffness of around 4000 lbs./inch, (4 lbs./0.001" or about 0.7 Newtons/μm), consistent with the predicted ideal value.

With this design, the flex of hub 18 in Case A for the 36 Newtons (Nt) restoring force is around 50 μm, or more than the peak-to-peak stroke length of 40 μm but less than 1.5 times the peak-to-peak stroke length. Laboratory experience indicates that this level of compliance can be tolerated.

It can be appreciated that the spring action at the joint 20, combined with the mass of the cannula, forms a mass-spring system with a resonant frequency for the needle assembly. For such a lumped model, the harmonic resonant frequency $\omega_0$ is known to be $\omega_0 = \sqrt{(k/m)}$. For the example given above, k~930000 Nt/m, m~0.000056 kg, $\omega_0$~128,000 radians/sec, and the resonant frequency is ~20 kHz. The stiffer the joint, the higher the resonant frequency of the needle assembly. As noted above, resonant frequencies of the needle assembly that are at least half the planned drive frequency can be tolerated, but needle assembly resonant frequencies equal to or greater than the planned drive frequency are preferred.

As with hub strength, hub stiffness is more important for ultrasonically driven needle assemblies than for injection needle assemblies. If an injection needle assembly shifts slightly forward during an injection, the deflection does not affect the quality of the injection, and many injection needle assemblies are mounted onto sterile plastic syringes, which are, themselves, quite compliant. However, unwanted or excessive deflection for an ultrasonic needle assembly may be ineffective or possibly dangerous. Hub design stiffness can be conveniently evaluated at the same time as hub design strength, by observing the needle assembly displacement as the axial force increases on an automated tensile strength tester, as referenced above, at forces below the failure force. The slope of the resulting stress/displacement curve represents the hub design stiffness. However, it should be noted that the measurement system should be significantly stiffer than the expected joint stiffness for reliable data. If the measurement system is not sufficiently stiff, the measured compliance will be somewhat less than the actual compliance.

An additional benefit of designing the hub to be stiff is a reduction in hub heating compared to a more compliant hub.

The compliant hub can be treated as a spring. The energy stored in the spring at maximum extension is a function of the force being applied and the spring constant. In practice, a portion of that energy is absorbed and dissipated by the spring each cycle creating heat and causing the spring to gradually heat up. Designing hubs that are relatively stiff (so they do not store as much energy in each force cycle) and selecting materials that have low mechanical dissipation loss factors (so that they do not absorb the energy as they stretch) and thermally stable mechanical properties (so that the performance does not change if the hub material heats up due to cyclical actuation) will result in improved performance of the needle assembly.

An alternate example description of a surgical needle assembly for attachment to an ultrasonic handpiece may be an elongated metal cannula having a distal end and a proximal end, as described above. A hub, as described above, is insert molded onto the cannula generally towards the cannula proximal end and formed from a material having an endurance strength equal to or greater than a peak cyclical stress force at a joint between the elongated metal cannula and the hub when the surgical needle assembly is in use with the ultrasonic handpiece. The hub material may also have a stiffness sufficient to limit a motion of the elongated metal cannula to less than 1.5 times an expected peak to peak stroke length when the surgical needle assembly is in use with the ultrasonic handpiece. The hub may also include a male structure for mating attachment to a female structure of the ultrasonic handpiece. The alternate example may have the same features and be formed of the same materials as described above.

Another alternate example description of a surgical needle assembly for attachment to an ultrasonic handpiece may be an elongated metal cannula having a distal end and a proximal end. A hub is insert molded onto the cannula generally towards the cannula proximal end and formed from a material having an endurance strength equal to or greater than a peak cyclical stress force at a joint between the elongated metal cannula and the hub when the surgical needle assembly is in use with the ultrasonic handpiece. The surgical needle assembly has a resonant frequency that is at least half of a nominal operating frequency of the ultrasonic handpiece. The hub includes a male structure for mating attachment to a female structure of the ultrasonic handpiece. Again, this alternate example may have the same features and be formed of the same materials as described above.

Still another alternate example may be described with respect to an ultrasonic surgical handpiece having a body. An ultrasonic vibration assembly is held within the body. A surgical needle assembly is attached to a distal portion of the ultrasonic vibration assembly. The surgical needle assembly includes an elongated metal cannula having a distal end and a proximal end. A hub is insert molded onto the cannula generally towards the cannula proximal end and formed from a material having an endurance strength equal to or greater than a peak cyclical stress force at a joint between the elongated metal cannula and the hub when the surgical needle assembly is in use with the ultrasonic handpiece. The surgical needle assembly has a resonant frequency that is at least half of a nominal operating frequency of the ultrasonic handpiece. The hub includes a male structure for mating attachment to a female structure of the ultrasonic handpiece. Again, the surgical needle assembly of this alternate example may have the same features and be formed of the same materials as described above. The ultrasonic vibration assembly may be piezoelectric or magneto-resistive assemblies that are well-known, such as shown in FIG. 7 at 35.

Yet another alternate example may be described with respect to an ultrasonic surgical handpiece having a body. An ultrasonic vibration assembly held within the body. An elongated metal cannula is insert molded onto a distal portion of the ultrasonic vibration assembly. In this alternate example, the hub may be formed and insert molded with the ultrasonic surgical handpiece and the elongated metal cannula simultaneously. That is the male structure described above is not formed prior to attachment to the handpiece and then threaded or press-fit onto the handpiece, rather the male structure is formed on the elongated metal cannula and attached to the handpiece by injection molding. For example, the hub 18 of FIG. 6 could be attached to cannula 12 and horn 32 via injection molding rather than the press-fit example described above.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms.

These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A surgical needle assembly for attachment to an ultrasonic handpiece comprising:
    an elongated metal cannula having a distal end and a proximal end;
    a hub insert molded onto the cannula generally towards the cannula proximal end and formed from a material having an ultimate strength at least twice a peak cyclical stress force at a joint between the elongated metal cannula and the hub when the surgical needle assembly is in use with the ultrasonic handpiece;
    wherein the hub material has a stiffness sufficient to limit a motion of the elongated metal cannula to less than 1.5 times an expected peak to peak stroke length when the surgical needle assembly is in use with the ultrasonic handpiece; and
    wherein the hub includes structure for mating attachment to the ultrasonic handpiece.

2. The surgical needle assembly of claim 1 wherein the elongated metal cannula further includes attachment structure formed on the cannula for enhancing an adhesion of the hub to the cannula.

3. The surgical needle assembly of claim 1 wherein the elongated metal cannula is formed from one of stainless steel and titanium.

4. The surgical needle assembly of claim 1 wherein the hub is formed from one of polyetherimide, polyaryletherketone, polysulfone, polyethersulfone, and polyphenylsulfone.

5. The surgical needle assembly of claim 1 wherein the hub includes a flange portion that is sufficiently thick for producing a liquid-tight seal with the ultrasonic handpiece.

6. The surgical needle assembly of claim 1 wherein the hub mating structure includes male threads formed in the hub.

7. The surgical needle assembly of claim 6 wherein the surgical needle assembly is attached to the ultrasonic handpiece via the threads and further includes a thread fill material for enhancing the attachment of the surgical needle assembly to the ultrasonic handpiece and enhancing a liquid-tight seal with the ultrasonic handpiece.

8. A surgical needle assembly for attachment to an ultrasonic handpiece comprising:
    an elongated metal cannula having a distal end and a proximal end;
    a hub insert molded onto the cannula generally towards the cannula proximal end and formed from a material having an endurance strength equal to or greater than a peak cyclical stress force at a joint between the elongated metal cannula and the hub when the surgical needle assembly is in use with the ultrasonic handpiece;
    wherein the hub material has a stiffness sufficient to limit a motion of the elongated metal cannula to less than 1.5 times an expected peak to peak stroke length when the surgical needle assembly is in use with the ultrasonic handpiece; and
    wherein the hub includes structure for mating attachment to the ultrasonic handpiece.

9. The surgical needle assembly of claim 8 wherein the elongated metal cannula further includes attachment structure formed on the cannula for enhancing an adhesion of the hub to the cannula.

10. The surgical needle assembly of claim 8 wherein the elongated metal cannula is formed from one of stainless steel and titanium.

11. The surgical needle assembly of claim 8 wherein the hub is formed from one of polyetherimide, polyaryletherketone, polysulfone, polyethersulfone, and polyphenylsulfone.

12. The surgical needle assembly of claim 8 wherein the hub includes a flange portion that is sufficiently thick for producing a liquid-tight seal with the ultrasonic handpiece.

13. The surgical needle assembly of claim 8 wherein the hub mating structure includes male threads formed in the hub.

14. The surgical needle assembly of claim 13 wherein the surgical needle assembly is attached to the ultrasonic handpiece via the threads and further includes a thread fill material for enhancing the attachment of the surgical needle assembly to the ultrasonic handpiece and enhancing a liquid-tight seal with the ultrasonic handpiece.

15. A surgical needle assembly for attachment to an ultrasonic handpiece comprising:
    an elongated metal cannula having a distal end and a proximal end;
    a hub insert molded onto the cannula generally towards the cannula proximal end and formed from a material having an endurance strength equal to or greater than a peak cyclical stress force at a joint between the elongated metal cannula and the hub when the surgical needle assembly is in use with the ultrasonic handpiece;
    wherein the surgical needle assembly has a resonant frequency that is at least half of a nominal operating frequency of the ultrasonic handpiece; and
    wherein the hub includes structure for mating attachment to the ultrasonic handpiece.

16. The surgical needle assembly of claim 15 wherein the elongated metal cannula further includes attachment structure formed on the cannula for enhancing an adhesion of the hub to the cannula.

17. The surgical needle assembly of claim 15 wherein the elongated metal cannula is formed from one of stainless steel and titanium.

18. The surgical needle assembly of claim 15 wherein the hub is formed from one of polyetherimide, polyaryletherketone, polysulfone, polyethersulfone, and polyphenylsulfone.

19. The surgical needle assembly of claim 15 wherein the hub includes a flange portion that is sufficiently thick for producing a liquid-tight seal with the ultrasonic handpiece.

20. The surgical needle assembly of claim 15 wherein the hub mating structure includes male threads formed in the hub.

21. The surgical needle assembly of claim 20 wherein the surgical needle assembly is attached to the ultrasonic handpiece via the threads and further includes a thread fill material for enhancing the attachment of the surgical needle assembly to the ultrasonic handpiece and enhancing a liquid-tight seal with the ultrasonic handpiece.

* * * * *